(12) United States Patent
Ruchala et al.

(10) Patent No.: US 7,839,972 B2
(45) Date of Patent: Nov. 23, 2010

(54) SYSTEM AND METHOD OF EVALUATING DOSE DELIVERED BY A RADIATION THERAPY SYSTEM

(75) Inventors: Kenneth J. Ruchala, Madison, WI (US); Gustavo H. Olivera, Madison, WI (US); Eric Schnarr, McFarland, WI (US); Weiguo Lu, Madison, WI (US); Thomas R. Mackie, Verona, WI (US)

(73) Assignee: Tomotherapy Incorporated, Madison, WI (US)

( * ) Notice: Subject to any disclaimer, the term of this patent is extended or adjusted under 35 U.S.C. 154(b) by 1110 days.

(21) Appl. No.: 11/459,097

(22) Filed: Jul. 21, 2006

(65) Prior Publication Data

US 2007/0195929 A1 Aug. 23, 2007

Related U.S. Application Data

(60) Provisional application No. 60/701,588, filed on Jul. 22, 2005, provisional application No. 60/701,580, filed on Jul. 22, 2005.

(51) Int. Cl.
*A61N 5/10* (2006.01)

(52) U.S. Cl. .......................................... 378/65

(58) Field of Classification Search ................. 600/315, 600/407, 427; 382/128, 130, 131, 132, 256, 382/257, 294
See application file for complete search history.

(56) References Cited

U.S. PATENT DOCUMENTS

| | | | |
|---|---|---|---|
| 3,949,265 A | 4/1976 | Holl | |
| 3,964,467 A | 6/1976 | Rose | |
| 4,006,422 A | 2/1977 | Schriber | |
| 4,032,810 A | 6/1977 | Eastham et al. | |
| 4,149,081 A | 4/1979 | Seppi | |
| 4,181,894 A | 1/1980 | Pottier | |
| 4,189,470 A | 2/1980 | Rose | |

(Continued)

FOREIGN PATENT DOCUMENTS

CA 2091275 9/1993

(Continued)

OTHER PUBLICATIONS

Ronald D. Rogus et al., "Accuracy of a Photogrammetry-Based Patient Positioning and Monitoring System for Radiation Therapy," Medical Physics, vol. 26, Issue 5, May 1999.

(Continued)

*Primary Examiner*—Brian Casler
*Assistant Examiner*—Elmer Chao
(74) *Attorney, Agent, or Firm*—Michael Best & Friedrich LLP (57) ABSTRACT

A system and method of evaluating dose delivered by a radiation therapy system using a marker that indicates motion. The marker is associated with the patient. In one method of operation, the method includes delivering radiation to the patient, monitoring motion of the marker during the delivering radiation, and evaluating a dose delivered to the patient based at least in part on the motion of the marker. In another method of operation, the method includes delivering radiation to the patient, obtaining information relating to the delivery of radiation, estimating dose to the marker based at least in part on the information, acquiring dose received by the marker, and comparing the received dose with the estimated dose.

24 Claims, 6 Drawing Sheets

U.S. PATENT DOCUMENTS

| | | |
|---|---|---|
| 4,208,185 A | 6/1980 | Sawai et al. |
| 4,273,867 A | 6/1981 | Lin et al. |
| 4,314,180 A | 2/1982 | Salisbury |
| 4,335,465 A | 6/1982 | Christiansen et al. |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,124,658 A | 6/1992 | Adler |
| 5,210,414 A | 5/1993 | Wallace et al. |
| 5,250,388 A | 10/1993 | Schoch et al. |
| 5,317,616 A | 5/1994 | Swerdloff et al. |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden |
| 5,442,675 A | 8/1995 | Swerdloff et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,523,578 A | 6/1996 | Herskovic |
| 5,528,650 A | 6/1996 | Swerdloff et al. |
| 5,548,627 A | 8/1996 | Swerdloff et al. |
| 5,576,602 A | 11/1996 | Hiramoto et al. |
| 5,578,909 A | 11/1996 | Billen |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,811,944 A | 9/1998 | Sampayan et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,834,454 A | 11/1998 | Kitano et al. |
| 5,836,905 A | 11/1998 | Lemelson et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,152,599 A | 11/2000 | Salter |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,316,776 B1 | 11/2001 | Hiramoto et al. |
| 6,319,469 B1 | 11/2001 | Mian et al. |
| 6,322,249 B1 | 11/2001 | Wofford et al. |
| 6,331,194 B1 | 12/2001 | Elizondo-Decanini et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |

| Patent | Date | Inventor |
|---|---|---|
| 6,407,505 B1 | 6/2002 | Bertsche |
| 6,417,178 B1 | 7/2002 | Klunk et al. |
| 6,424,856 B1 | 7/2002 | Vilsmeier et al. |
| 6,428,547 B1 | 8/2002 | Vilsmeier et al. |
| 6,433,349 B2 | 8/2002 | Akiyama et al. |
| 6,438,202 B1 | 8/2002 | Olivera et al. |
| 6,455,844 B1 | 9/2002 | Meyer |
| 6,462,490 B1 | 10/2002 | Matsuda et al. |
| 6,465,957 B1 | 10/2002 | Whitham et al. |
| 6,466,644 B1 | 10/2002 | Hughes et al. |
| 6,469,058 B1 | 10/2002 | Grove et al. |
| 6,472,834 B2 | 10/2002 | Hiramoto et al. |
| 6,473,490 B1 | 10/2002 | Siochi |
| 6,475,994 B2 | 11/2002 | Tomalia et al. |
| 6,482,604 B2 | 11/2002 | Kwon |
| 6,484,144 B2 | 11/2002 | Martin et al. |
| 6,487,274 B1 | 11/2002 | Bertsche |
| 6,493,424 B2 | 12/2002 | Whitham |
| 6,497,358 B1 | 12/2002 | Walsh |
| 6,498,011 B2 | 12/2002 | Hohn et al. |
| 6,500,343 B2 | 12/2002 | Siddiqi |
| 6,504,899 B2 | 1/2003 | Pugachev et al. |
| 6,510,199 B1 | 1/2003 | Hughes et al. |
| 6,512,942 B1 | 1/2003 | Burdette et al. |
| 6,516,046 B1 | 2/2003 | Frohlich et al. |
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,723,334 B1 | 4/2004 | McGee et al. |
| 6,760,402 B2 | 7/2004 | Ghelmansarai |
| 6,774,383 B2 | 8/2004 | Norimine et al. |
| 6,787,771 B2 | 9/2004 | Garty et al. |
| 6,787,983 B2 | 9/2004 | Yamanobe et al. |
| 6,788,764 B2 | 9/2004 | Saladin et al. |
| 6,792,073 B2 | 9/2004 | Deasy et al. |
| 6,796,164 B2 | 9/2004 | McLoughlin et al. |
| 6,800,866 B2 | 10/2004 | Amemiya et al. |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 | 1/2005 | Jaffray et al. |
| 6,844,689 B1 | 1/2005 | Brown et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 | 5/2005 | Pankratov et al. |
| 6,922,455 B2 | 7/2005 | Jurczyk et al. |
| 6,929,398 B1 | 8/2005 | Tybinkowski et al. |
| 6,936,832 B2 | 8/2005 | Norimine et al. |
| 6,955,464 B1 | 10/2005 | Tybinkowski et al. |
| 6,963,171 B2 | 11/2005 | Sagawa et al. |
| 6,974,254 B2 | 12/2005 | Paliwal et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,112,924 B2 | 9/2006 | Hanna |
| 7,130,372 B2 | 10/2006 | Kusch et al. |
| 7,154,991 B2 | 12/2006 | Earnst et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 | 4/2007 | Baier et al. |
| 7,221,733 B1 | 5/2007 | Takai et al. |
| 7,252,307 B2 | 8/2007 | Kanbe et al. |
| 7,257,196 B2 | 8/2007 | Brown et al. |
| 2002/0007918 A1 | 1/2002 | Owen et al. |
| 2002/0077545 A1 | 6/2002 | Takahashi et al. |
| 2002/0080915 A1 | 6/2002 | Frohlich |
| 2002/0085668 A1 | 7/2002 | Blumhofer et al. |
| 2002/0091314 A1 | 7/2002 | Schlossbauer et al. |
| 2002/0115923 A1 | 8/2002 | Erbel |
| 2002/0120986 A1 | 9/2002 | Erbel et al. |
| 2002/0122530 A1 | 9/2002 | Erbel et al. |
| 2002/0136439 A1 | 9/2002 | Ruchala et al. |
| 2002/0150207 A1 | 10/2002 | Kapatoes et al. |
| 2002/0187502 A1 | 12/2002 | Waterman et al. |
| 2002/0193685 A1 | 12/2002 | Mate et al. |
| 2003/0007601 A1 | 1/2003 | Jaffray et al. |
| 2003/0031298 A1 | 2/2003 | Xing |
| 2003/0086527 A1 | 5/2003 | Speiser et al. |
| 2003/0105650 A1 | 6/2003 | Lombardo et al. |
| 2003/0174872 A1 | 9/2003 | Chalana et al. |
| 2004/0010418 A1 | 1/2004 | Buonocore et al. |
| 2004/0068182 A1 | 4/2004 | Misra |
| 2004/0116804 A1 | 6/2004 | Mostafavi |
| 2004/0165696 A1 | 8/2004 | Lee |
| 2004/0202280 A1 | 10/2004 | Besson |
| 2004/0230115 A1 | 11/2004 | Scarantino et al. |
| 2004/0254492 A1 | 12/2004 | Zhang et al. |
| 2004/0254773 A1 | 12/2004 | Zhang et al. |
| 2004/0264640 A1 | 12/2004 | Myles |
| 2005/0013406 A1 | 1/2005 | Dyk et al. |
| 2005/0031181 A1 | 2/2005 | Bi et al. |
| 2005/0080332 A1 | 4/2005 | Shiu et al. |
| 2005/0096515 A1 | 5/2005 | Geng |
| 2005/0123092 A1 | 6/2005 | Mistretta et al. |
| 2005/0143965 A1 | 6/2005 | Failla et al. |
| 2005/0180544 A1 | 8/2005 | Sauer et al. |
| 2005/0197564 A1 | 9/2005 | Dempsey |
| 2005/0251029 A1 | 11/2005 | Khamene et al. |
| 2006/0074292 A1 | 4/2006 | Thomson et al. |
| 2006/0083349 A1 | 4/2006 | Harari et al. |
| 2006/0100738 A1 | 5/2006 | Alsafadi et al. |
| 2006/0133568 A1 | 6/2006 | Moore |
| 2006/0193429 A1 | 8/2006 | Chen |
| 2006/0193441 A1 | 8/2006 | Cadman |
| 2006/0285639 A1 | 12/2006 | Olivera et al. |
| 2007/0041494 A1 | 2/2007 | Ruchala et al. |

| | | | |
|---|---|---|---|
| 2007/0041495 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0088573 A1 | 4/2007 | Ruchala et al. | |
| 2007/0104316 A1 | 5/2007 | Ruchala et al. | |
| 2007/0127623 A1 | 6/2007 | Goldman et al. | |
| 2007/0189591 A1 | 8/2007 | Lu et al. | |
| 2007/0195922 A1 | 8/2007 | Mackie et al. | |
| 2007/0195930 A1 | 8/2007 | Kapatoes et al. | |
| 2007/0201613 A1 | 8/2007 | Lu et al. | |

FOREIGN PATENT DOCUMENTS

| | | |
|---|---|---|
| CA | 2180227 | 12/1996 |
| TW | 261523 | 9/2006 |
| WO | 2004057515 | 7/2004 |

OTHER PUBLICATIONS

D. Rueckert et al., "Nonrigid Registration Using Free-Form Deformations: Application to Breast MR Images," IEEE Transactions on Medical Imaging, vol. 18, No. 8, Aug. 1999.

Yuan-Nan Young, "Registraion-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001.

Karen Miller, "The Phantom Torso", RT Image, vol. 14 No. 25, Jun. 18, 2001.

SYSTEM AND METHOD OF EVALUATING DOSE DELIVERED BY A RADIATION THERAPY SYSTEM

RELATED APPLICATIONS

This application claims the benefit of U.S. Provisional Patent Application No. 60/701,588; titled SYSTEM AND METHOD OF DETERMINING POSITION OF AN OBJECT AND DELIVERING RADIATION THERAPY TREATMENT; filed on Jul. 22, 2005; and the benefit of U.S. Provisional Patent Application No. 60/701,580; filed Jul. 22, 2005; titled SYSTEM AND METHOD FOR FEEDBACK GUIDED QUALITY ASSURANCE AND ADAPTATIONS TO RADIATION THERAPY TREATMENT; both of which are incorporated herein by reference.

BACKGROUND

Over the past decades, improvements in computers and networking, radiation therapy treatment planning software, and medical imaging modalities (CT, MRI, US, and PET) have been incorporated into radiation therapy practice. Often, devices are used to track the motion and position of the equipment that is used to deliver a treatment. The amount of radiation that is delivered to a patient during a treatment is also monitored in order to deliver the correct dose (e.g., amount of radiation) to the appropriate target treatment area. Typically, equipment and patient position information is gathered via mechanical sensors that are hard-wired to control computers.

SUMMARY

In one embodiment, the invention provides a local positioning system ("LPS"), to control, verify, synchronize, and/or QA radiation therapy treatment systems or imaging device systems. This can be done in real-time or as a post-process. An aspect of the invention includes an interface between the LPS and other positioning systems, and the use of this information for machine control, synchronization, and/or patient procedures, such as imaging or therapy. In another aspect, the LPS can communicate with other patient monitoring devices to acquire information to use for machine control, synchronization, and/or patient procedures.

Another embodiment of the invention includes a method for tracking different hardware components in the context of patient imaging or treatment. These components can include gantries, couches, collimators (both the base and/or individual leaves) or other components for which feedback is desired. Sensors for this system could also be affixed to patients.

One method of positioning feedback utilizes mechanical sensors that are typically hard-wired to control computers. Other methods of feedback focus on patient monitoring, and these include implantable RF devices that can be inserted into the patient. Some of these devices use MOSFET technology to provide feedback on dose received, while others provide readout of location.

In another embodiment, the invention provides a radiation imaging and/or therapy-treatment system. The system comprises a radiation source, a movable apparatus, a controller configured to control, including moving, the movable apparatus, and a local positioning system. The local position system includes a position verification device directly coupled to the movable apparatus and a system monitoring module in communication with the position verification device. The local positioning system is configured to determine position data for the position verification device.

In another embodiment, the invention provides a method of evaluating dose delivered by a radiation therapy system using a marker that indicates motion. The marker is associated with the patient. The method comprises the acts of delivering radiation to the patient, monitoring motion of the marker during the delivering radiation, and evaluating a dose delivered to the patient based at least in part on the motion of the marker.

In another embodiment, the invention provides a method of evaluating dose delivered by a radiation therapy system using a marker associated with the patient. The method comprises the acts of delivering radiation to the patient, obtaining information relating to the delivery of radiation, estimating dose to the marker based at least in part on the information, acquiring dose received by the marker, and comparing the received dose with the estimated dose.

In another embodiment, the invention proves a method of evaluating dose delivered by a radiation therapy system using a marker that indicates motion. The marker is associated with the patient. The method comprises the acts of delivering radiation to the patient, monitoring motion of the marker during the delivering radiation, estimating a dose delivered to the patient based at least in part on the motion of the marker, acquiring dose received by the marker, and comparing the received dose with the estimated dose.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the invention in any form. In addition, terms such as "first", "second", and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
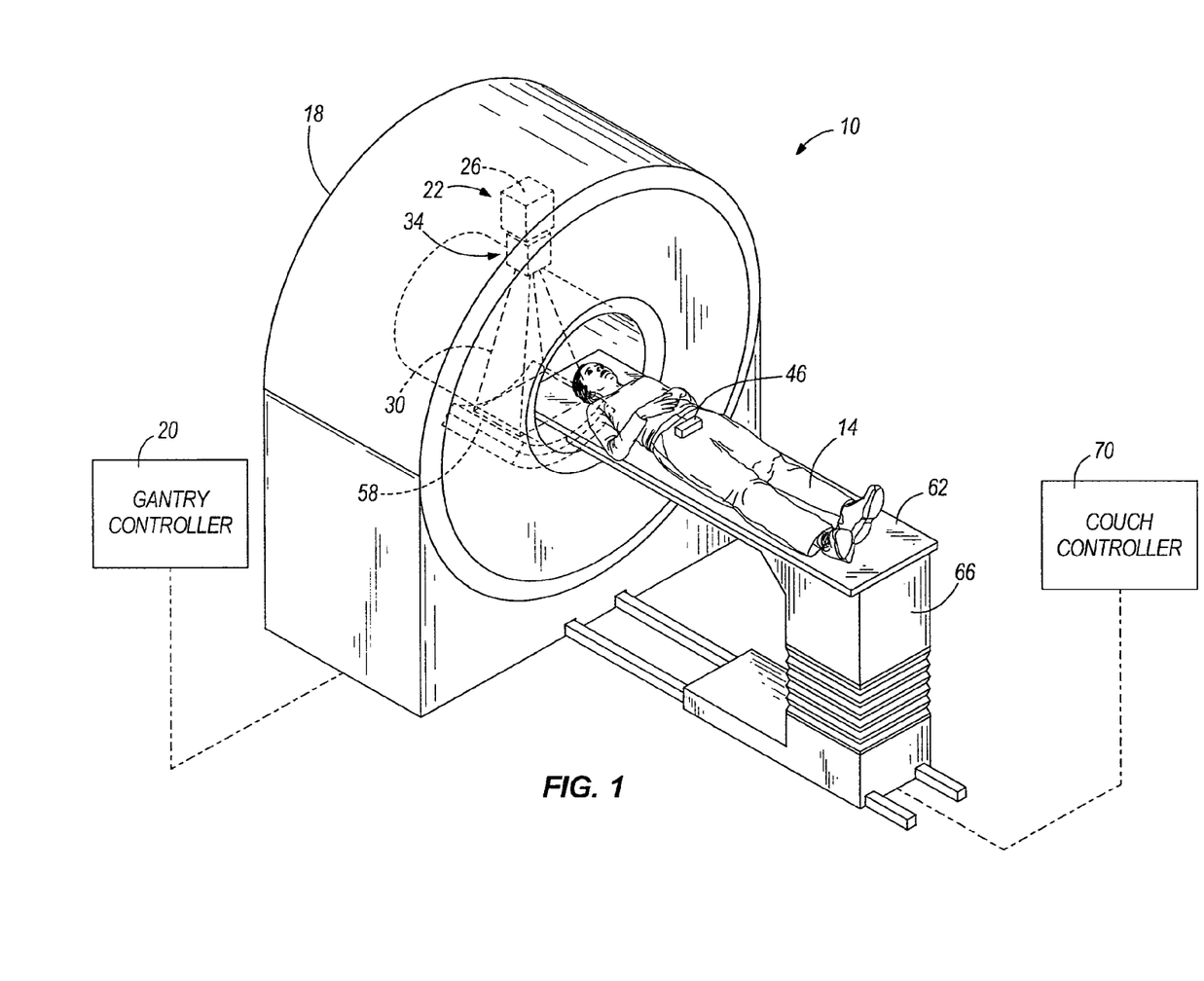
FIG. 1 is a partial perspective view, partial schematic illustration of a radiation therapy treatment system according to one embodiment of the invention.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a radiation therapy device having a gantry 18 controlled by to a gantry controller 20. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used.

The gantry 18 can support a radiation module, having a radiation source 22 and a linear accelerator 26 operable to generate a beam 30 of photon radiation. The radiation module can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target or target region (shown as 46), is an example of a region of interest. Another type of region of interest is a region at risk. If a portion includes a region at risk, the radiation beam is preferably diverted from the region at risk. The patient 14 may have more than one target region 46 that needs to receive radiation therapy. Such modulation is sometimes referred to as intensity modulated radiation therapy ("IMRT").

Other frameworks capable of positioning the radiation module at various rotational and/or axial positions relative to the patient 14 may also be employed. In addition, the radiation source 22 may travel in path that does not follow the shape of the gantry 18. For example, the radiation source 24 may travel in a non-circular path even though the illustrated gantry 18 is generally circular-shaped.

Figure 2:
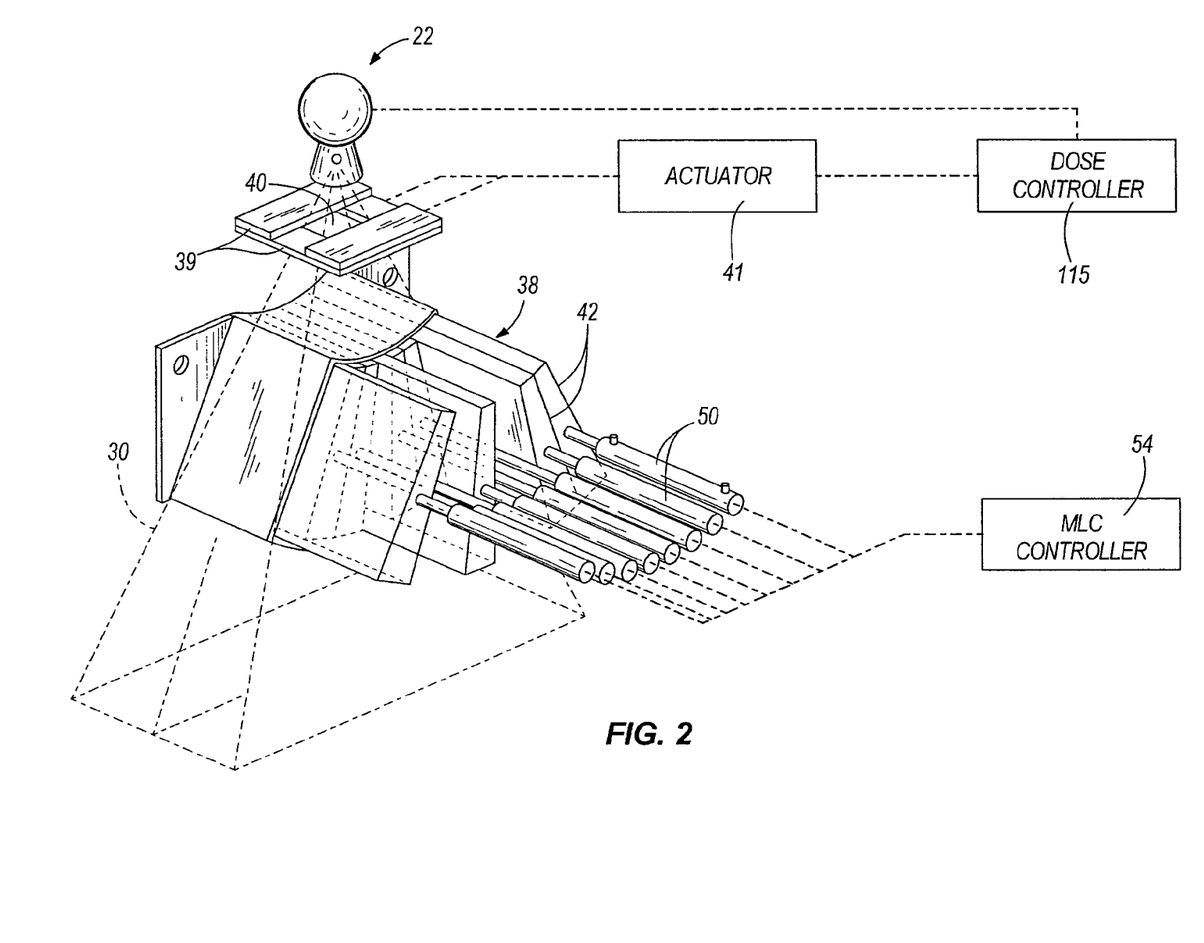
FIG. 2 is a partial perspective view, partial schematic illustration of a multi-leaf collimator that can be used in the radiation therapy treatment system illustrated in FIG. 1.

In one construction, and illustrated in FIG. 2, the modulation device 34 includes a collimation device. The collimation device includes the primary collimator having a set of jaws 39. The jaws define and adjust the size of an aperture 40 through which the radiation beam 30 may pass. The jaws 39 include an upper jaw and a lower jaw controlled by an actuator 41. The upper jaw and the lower jaw are moveable to adjust the size of the aperture 40. The collimation device further includes a multi-leaf collimator (MLC) 38, which includes a plurality of interlaced leaves 42 operable to move from position to position. The movement of the leaves 42 and jaws 39 can be tracked with positioning devices (as described in greater detail below). It is also noted that the leaves 42 can be moved to a position anywhere between a minimally and maximally-open position. The plurality of interlaced leaves 42 modulates the strength, size, and shape of the radiation beam 30 before the radiation beam 30 reaches the target 46 on the patient 14. Each of the leaves 42 is independently controlled by an actuator 50, such as a motor or an air valve so that the leaf 42 can open and close quickly to permit or block the passage of radiation. The actuators 50 can be controlled by a MLC computer and/or controller 54.

The radiation therapy treatment system 10 (FIG. 1) can also include a detector 58 (e.g., a kilovoltage or a megavoltage detector) operable to receive a radiation beam from the treatment radiation source 22 or from a separate radiation source. The linear accelerator 26 and the detector 58 can also operate as a computed tomography ("CT") system to generate CT images of the patient 14. The linear accelerator 26 emits the radiation beam 30 toward the target 46 in the patient 14. The CT images can be acquired with a radiation beam 30 that has a fan-shaped geometry, a multi-slice geometry, or a cone-beam geometry. In addition, the CT images can be acquired with the linear accelerator 26 delivering megavoltage energies or kilovoltage energies. The target 46 and surrounding tissues absorb some of the radiation. The detector 58 detects or measures the amount of radiation absorbed by the target 46 and the surrounding tissues. The detector 58 collects the absorption data from different angles as the linear accelerator 26 rotates around and emits radiation toward the patient 14. The collected absorption data is transmitted to the computer 54 to process the absorption data and to generate cross-sectional images or "slices" of the patient's body tissues and organs. The images can also illustrate bone, soft tissues and blood vessels.

The radiation therapy treatment system 10 can also include a patient support, such as a couch 62 (illustrated in FIG. 1), which supports the patient 14. The couch 62 moves along at least one axis in the x, y, or z directions. In other constructions, the patient support can be a device that is adapted to support any portion of the patient's body, and is not limited to having to support the entire patient's body. The system 10 also can include a drive system 66 operable to manipulate the position of the couch 70. The drive system 66 can be controlled by a couch computer and/or controller 70. Alternatively, the drive system 66 can be controlled using another computer and/or controller of the treatment system 10.

The radiation therapy treatment system 10, as described above, includes many components and mechanisms (e.g., the couch 62, the MLC 38, the gantry 18, etc.) that can move from one position to another in order to deliver a desired dose (e.g., a predetermined amount of radiation) to the patient 14. For example, the leaves 42 of the MLC 38 can move in order to modulate the intensity of radiation that is being delivered to the patient 14. Additionally, the couch 62 can move in order to properly position the target 46. The motion of each of the components of the treatment system 10, therefore, can be precisely controlled to deliver the proper dose to the patient 14. The motions (as well as operations) of the components and mechanisms of the treatment system 10 can be controlled with a plurality of computers and/or controllers (e.g., the gantry controller 20, the couch controller 70, the MLC controller 54, etc.). Other controllers, such as a dose controller 75 (shown in FIG. 3), can also be implemented to deliver the proper dose to the patient 14 during the treatment. The dose controller 75 can receive signals from a plurality of positioning and dose verification devices (as described in greater detail below) in order to determine the proper dose that is to be delivered to the patient 14.

Alternatively, a single system computer (not shown) can be used to control the entire treatment system 10, which incorporates the processes and operations of all of the separate controllers and/or computers.

Figure 3:
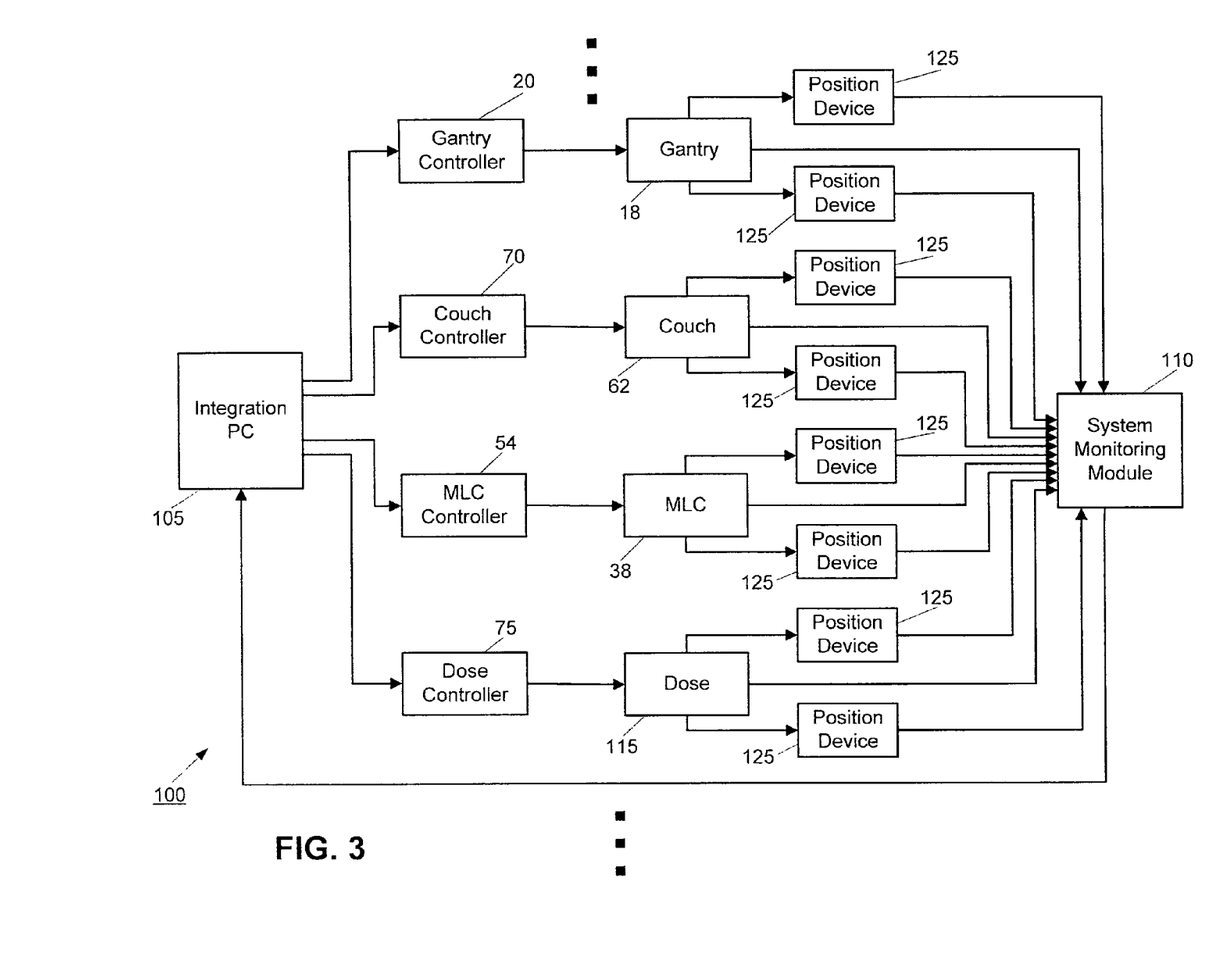
FIG. 3 schematically illustrates a local positioning system according to one embodiment of the invention and incorporated with the radiation therapy treatment system of FIG. 1.

FIG. 3 illustrates an embodiment of a LPS 100, having links to multiple radiation therapy treatment system components, as well as their respective controllers. The LPS 100 can also be used to track the movement of the patient 14 and target 46 (as described with respect to FIG. 4). In other embodiments, the LPS 100 can be implemented in other types of imaging equipment (e.g., CT, MRI, PET, etc.), and is not limited to the radiation therapy treatment system 10 that is shown in FIG. 1. In the embodiment shown in FIG.3, the LPS 100 includes an integration computer 105, a system monitoring module 110, and a plurality of position verification devices 125.

Before proceeding further, it should be understood that the plurality of position verification devices 125 may also be referred to herein as the plurality of motion verification devices 125. As discussed herein, the position verification devices 125 can be used to acquire a velocity (or speed), an acceleration, or a time series for the devices 125. The position information, velocity information, acceleration information, and time series information can be collectively referred to herein as motion information, hence the possible use of the term "motion verification device" in alternative to "position verification device." Also as discussed herein, the position verification devices 125 (or motion verification devices 125) can be used to monitor radiation to the position verification devices 125.

As shown in FIG. 3, each of the controllers of the treatment system 10 (e.g., the gantry controller 20, the couch controller 70, the MLC controller 54, the dose controller 75, etc.) can transmit signals to each of their respective treatment system components in order to control their motion and operation. It should be understood that signals, such as those being received and transmitted in FIG. 3, can be sustained with wired and wireless communication components (e.g., a copper wire, a coaxial cable, a radio frequency ("RF"), an infrared ("IR") signal, a Wi-Fi signal, etc.). The treatment system components also transmit signals to the system monitoring module 110. Those signals can correspond to the actual position and operation of the components. The system monitoring module 110 can also receive signals from the position verification devices 125.

Referring still to FIG. 3, the position verification devices 125 of the LPS 100 can be coupled to various components of the treatment system 10. The position verification devices 125 can be used to gather relative and absolute position data from the components of the treatment system 10, which can aid in optimizing the delivery of a radiation therapy treatment. For example, a position verification device 125 can be coupled to the couch 62 to provide a position, speed, and/or sag of the couch 62. As other examples, the position verification devices 125 can be strategically located to detect gantry position, speed, and sag and leaf position and speed.

The position verification device 125 can also supply position data that is relative to other components, for example, the couch position relative to the gantry position. Similarly, position verification devices 125 can be coupled to various other components (e.g., the leaves 42 of the MLC 38, the gantry 18, the linear accelerator 26, etc) of the treatment system 10 in order to provide other position data. Additionally, in some embodiments, positioning devices and beacons can be coupled to, or implanted in patients 14 to provide patient 14 and target position information (as described in greater detail with respect to FIG. 4).

In some embodiments, the LPS 100 can also be used to track the speed at which the components of the treatment system 10 are moving. More specifically, the speed of the components can be determined in a variety of methods by using the signals of the position verification devices 125. In one embodiment, the Doppler Effect is used to track the speed of each of moving components. In another embodiment, a position/time comparison calculation can be completed to determine the speed of each component of the treatment system 10. For example, the speed with which the linear accelerator 26 moves from one position to another around the gantry 18 can be tracked using the Doppler Effect by tracking a position verification device 125 fixed to the linear accelerator.

In order to track the position and speed of each of the verification devices 125, the signals that are received by the system monitoring module 110 are relayed to the integration computer 105. In some embodiments, the signals that are transmitted to the integration computer 105 from the system monitoring module 110 are relayed directly and without alteration. In other embodiments, the signals that are transmitted from the system monitoring module 110 to the integration computer 105 are modulated or altered prior to being sent. Alternatively, the system monitoring module 110 can be incorporated directly into the integration computer 105.

Upon receiving the signals from the system monitoring module 110, the integration computer 105 can complete the control loop that is created by the LPS 100, and transmit signals back to each of the plurality of system controllers (i.e., the gantry controller 20, the couch controller 70, the MLC controller 54, the dose controller 75, etc.). The signals that are transmitted from the integration computer 105 to each of the system controllers can then be used to alter the position and operation of the system components. Therefore, the integration computer 105 can effectively control the entire treatment system 10.

In one embodiment, the integration computer 105 of the LPS 100 can be used to compare the signals (e.g., motion signals such as position signals, velocity signals, acceleration signals, etc.) of each of the treatment system components to the signals of the position verification devices 125. For example, the position signal of a position verification device 125 that is coupled to the couch 62 can be cross-checked with a hard-wired position signal that is transmitted directly from the couch 62. If the position verification device signal differs from the signal produced by the couch 62, the integration computer 105 can determine if an alteration to the couch position needs to be made. The integration computer 105 can then transmit a correction signal to the couch controller 70 in order to move the couch 62 to the proper position.

In another embodiment, the speed of a component can be corrected with the LPS 100 using the integration computer 105. For example, the speed that is monitored with the position verification devices 125 can be compared to a speed signal that is produced from a hard-wired component of the linear accelerator 26. If the speed that is monitored with the position verification device 125 differs from that of a hard-wired connection, an alteration to the motion of the linear accelerator 26 can be made using the integration computer 105.

The LPS 100, therefore, can be used to gather a plurality of information from components of the treatment system 10 in order to temporally and spatially monitor and correct the motion of each component using absolute and relative reference points. In doing so, each of the components of the treatment system 10 that are being tracked by the position verification devices 125 can be coordinated and synchronized with each other to deliver the proper dose and treatment to the patient 14. For example, the couch 62, the linear accelerator 26, and the MLC 42 can all be synchronized, and have their motions verified in real-time by the integration computer 105 to deliver a treatment to the patient 14. Corrections to speed and position of the components of the treatment system 10 can be made as needed.

In another embodiment, the LPS 100 and/or other object positioning systems can interface and/or communicate with the treatment system 10 to conduct post-processing verification operations. It is noted that patient monitoring devices could also interface and/or communicate with the treatment system 10 to perform post-processing verification operations. After a treatment is completed, the signals of the position verification devices 125 can be reviewed. The hard-wired signals of each of the components of the treatment system 10 can also be reviewed. The signals from the position verification devices 125 can then be compared to the corresponding hard-wired signals. The results of the comparison can be used as a quality assurance check to verify that all of the components of the treatment system 10 have operated correctly. Faulty components and components that need to be replaced can potentially be identified using this comparison.

Figure 4:
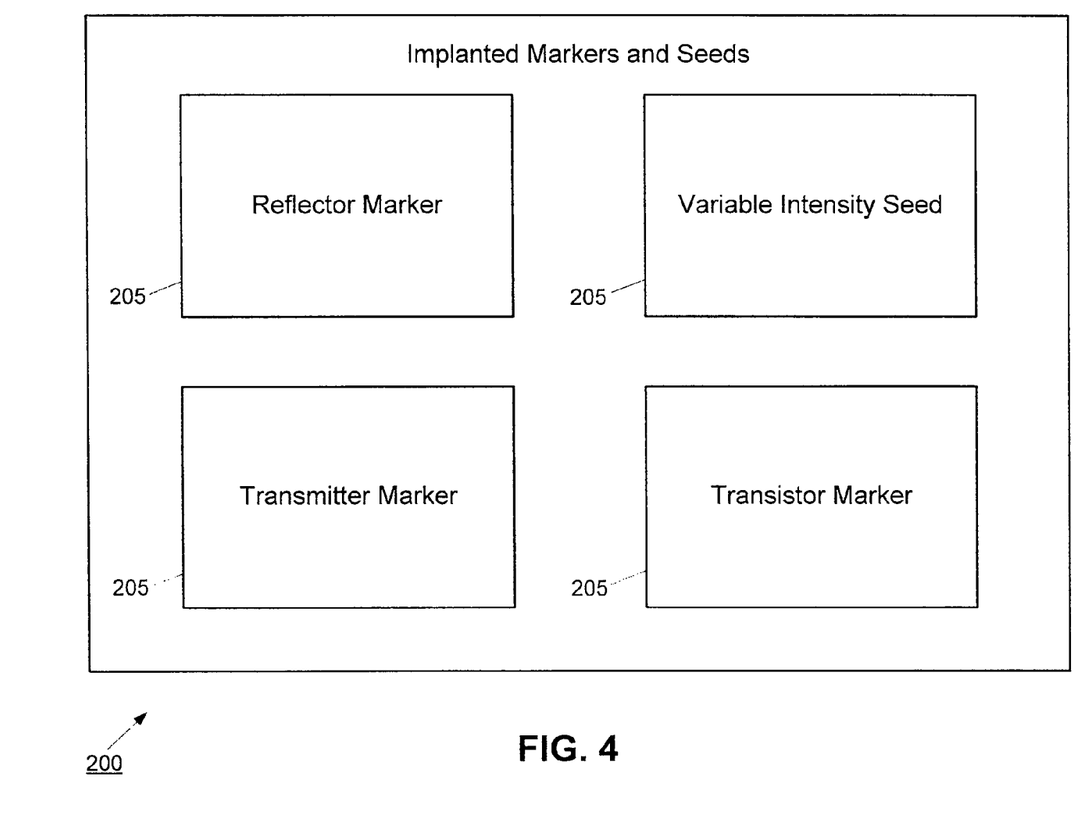
FIG. 4 is a block diagram of a plurality of devices that can be used in the local positioning system of FIG. 3.

The position verification devices 125 (described above) of the LPS 100 are not limited to monitoring mechanical devices and components (i.e., the gantry 18, the MLC 38, the couch 62, etc.). Also, the verification aspects of this invention are not limited to the LPS devices described above. In another embodiment, a plurality of position monitoring devices can be coupled to, or implanted in the patient 14 in order to monitor, detect, and/or alter the dose 115 that is delivered during a treatment. FIG. 4 illustrates a group 200 of exemplary position devices that can aid in the delivery of a radiation therapy treatment. The position devices can include a reflector marker 205, a transmitter marker 210, a variable intensity seed 215, and a transistor marker 220. Other types of position devices can include a radio-frequency seed and a variable frequency seed. Each of the position devices included in the group 200 can be incorporated into the LPS 100. In other embodiments, the position devices 205-220 need not be included in the LPS 100, and can be implemented in a separate, stand-alone monitoring system. Before proceeding further, it should be understood that the term "marker" is used broadly herein to encompass the term seed. For example, the variable intensity seed 215 may also be referred to herein as the variable intensity marker 215.

In some embodiments, reflector markers 205 are implanted near the target 46 of a patient 14, and used as a passive tracking and positioning beacon. The reflector markers 205 can also be positioned in a location that approximates the patient 14 (such as the couch 62). When the reflector marker 205 is excited by a trigger source, such as a radiation source, the position of the reflector marker 205 can be used to "local-ize" the position of the target 46. In some embodiments, the reflector markers are used in combination with CT imaging prior to, or during radiation treatment. The position data that is gained using the reflector markers 205 can confirm the patient 14 and target 46 locations with respect to the patient's anatomy. Therefore, the reflector markers can aid in directing the radiation therapy treatment toward the target 46. The reflector markers 205 can also be implanted in (or positioned near) other areas of the patient 14. For example, markers 205 can be implanted near an identified region at risk ("RAR") in order to avoid exposing a particularly vulnerable area to radiation.

Transmitter markers 210 are another type of localizer, and can be used similarly to the reflector markers 205. However, the transmitter markers 210 do not require a trigger source to be activated. Therefore, depending on the configuration, the transmitter marker 210 can be located at any time during a treatment (and not only when the patient is being exposed to radiation). Transmitter markers 210 can transmit a variety of signals (e.g., RF, Bluetooth, WiFi, IEEE 802.15.4, and the like), which are received by a corresponding receiver.

In another embodiment, variable intensity seeds 215 can be used to track both the position of the patient 14 and the dose that is delivered to the patient 14. For example, an RF localization seed can be configured to produce a specific signal, which corresponds to a certain predetermined dose that is to be delivered to the patient 14. The configured RF seed can then be implanted into or near the target 46 of the patient 14. Each time the RF seed is exposed to a radiation treatment, the RF signal that is transmitted from the seed can become weaker. After the entire predetermined dose has been delivered, the seed will stop transmitting signal.

For radiation treatments that require multiple delivery sessions, the variable intensity seeds 215 can be probed for information prior to every treatment. In doing so, the amount of radiation that has been delivered to the patient prior to that delivery session can be verified. Additionally, the amount of radiation that has been received by the seed 215 can be verified with the amount of radiation that has been delivered by the treatment system 10. Those values can then be compared, and the operation of the treatment system 10 can be verified. In other embodiments, the seeds 215 can transmit their variable signal using a plurality of other techniques (including wireless and wired connections), such as WiFi, signals included in the IEEE 802.15 family, fiber optic connections, or traditional wire connections. Additionally, the seeds 215 can be varied in alternative ways in order to determine the dose that is delivered to the patient 14. For example, in some embodiments, the signal that is transmitted from the seeds 215 can increase, or get stronger, according to the amount of radiation that is received.

In some embodiments, the variable intensity seeds 215 can aid in determining deformation of the target 46 (e.g., how the target 46 reacts to the radiation treatment). For example, the markers, such as the variable intensity seeds 215, can be used as fiduciary points for deformation calculations. Deformation calculations can be made initially using a CT image, or by tracking the target 46 with one or more markers. An example deformation calculation is described in U.S. Provisional Patent Application No. 60/701,580; filed Jul. 22, 2005; titled SYSTEM AND METHOD FOR FEEDBACK GUIDED QUALITY ASSURANCE AND ADAPTATIONS TO RADIATION THERAPY TREATMENT, the entire content of which is incorporated herein by reference. The deformation of the target 46 can then be compared to the amount of radiation that is delivered to the patient 14, which can be calculated using the seeds 215. Radiation treatment strategies may be altered according to the amount of radiation that is received when compared to the amount of deformation that has occurred.

Figure 5:
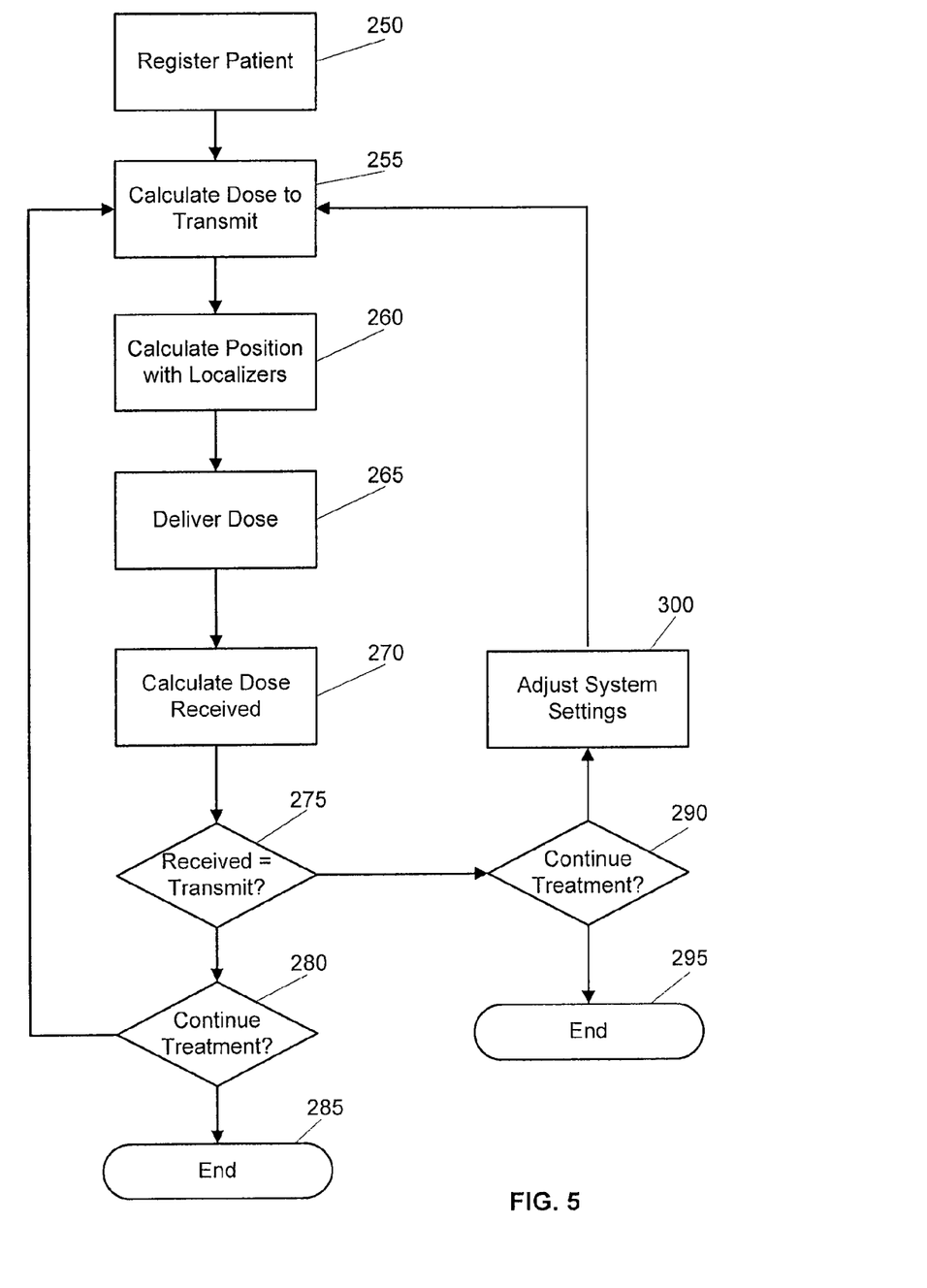
FIG. 5 is a flow chart of a method of delivering a radiation therapy treatment that utilizes variable intensity seeds according to one embodiment of the invention.

FIG. 5 illustrates a flow chart of a method of delivering a radiation therapy treatment that utilizes variable intensity seeds 215. The patient 14 is first registered by the treatment system 10 (block 250). To do so, the variable intensity seeds 215 can transmit registration signals that are unique to the patient 14 and the target 46, which can help ensure that the correct treatment is being delivered. Once registered, the dose that is to be delivered to the patient 14 can be determined (block 255). The intensity of the signal that is being transmitted from the seed(s) 215 may be adjusted according to the dose that is determined. The amount of radiation that is delivered in a dose can depend on the patient 14, the target 46, and the deformation of the target 46. After determining the dose that is to be delivered to the patient 14, the position of the target 46 can be determined (block 260). In some embodiments, the signal that is being transmitted from the seed 215 can be used to calculate the position of the target 46. In other embodiments, markers (such as markers 205 and 210) can be used to determine the location of the target 46. Additionally, the positions of other areas (e.g., the position of the patient's body on the couch 62) can also be tracked, as described above.

Once the position data has been collected, the predetermined dose can be delivered to the patient 14 (block 265). During delivery, the seeds 215 can be used to calculate the dose that is being received by the patient 14 (block 270). In some embodiments, the signal that is being transmitted from the seeds 215 is tracked continuously so that the amount of radiation that is being received by the patient can be tracked throughout a treatment. In other embodiments, the signal from the seeds 215 is read or polled at predetermined intervals. In order to verify that the correct dose is being received by the patient, the dose that is being delivered can be compared to the dose that is being received according to the seed 215 (block 275). If the amount of radiation that is being received by the patient 14 is relatively equal to the amount of radiation that is being delivered, a determination can be made whether or not to continue the treatment (block 280). The treatment can be ended (block 285) if the signal from the seed 215 is no longer present. However, if additional treatment is required, the process can return to block 255 in order to determine the proper dose to be delivered to the patient 14.

Referring again to block 275, if the amount of radiation that is being received by the patient 14 is not relatively equal to the amount of radiation that is being delivered by the treatment system 10, a determination whether or not to continue the treatment can be made (block 290). In some embodiments, a difference between the amount of radiation that is delivered to the patient 14 and the amount of radiation that is received by the patient 14 can signal a treatment system malfunction. Such a discrepancy may also be an indication that the improper area is being treated. In such embodiments, the treatment may be terminated (block 295). However, in some embodiments, adjustments can be made to alter the dose that is delivered, change position of the components of the treatment system 10, or change the position of the patient 14 (block 300). Such alterations can correct the delivery of the treatment so that the delivery can continue. After adjusting the necessary components, the process can return to block 255 so that the dose calculation can be completed for the subsequent delivery. An example dose calculation is also described in U.S. Provisional Patent Application No. 60/701,580.

In one embodiment, the process shown in FIG. 5 can be carried out using the dose controller 75 (illustrated in FIG. 3) that is included in the LPS 100. In another embodiment, the process shown in FIG. 5 can be implemented using a separate, stand-alone system. The speed with which the process steps are completed can depend on the capabilities of the system that is completing it. In some embodiments, the process is virtually continually updated so that the treatment system alterations to the dose and delivery can be made during a treatment.

Referring back to FIG. 4, transistor markers 220 can also be used to track the position of the patient 14, and the dose that is received by the patient 14. However, unlike the variable intensity seeds 215, the signal of the transistor markers 220 can be used to monitor the intensity of the dose, as well as the amount of radiation that has been received by the patient. More specifically, the intensity signals from the transistor markers 220 can be compiled to provide an indication of the dose that has been received by the patient 14.

In one embodiment, a metal-oxide-semiconductor field effect transistor ("MOSFET") marker 220, such as sensors or markers from Sicel Technologies, Inc. in Morrisville, N.C., can be used in combination with other localizer markers (such as markers 205 and 210) to aid in the optimized delivery of a dose to the patient 14. The localizer markers can be used to determine the location and deformation characteristics of the target 46, and the MOSFET marker 220 can be used to monitor the dose that is being received by the patient 14. The dose that is received by the patient 14, and tracked by the MOSFET marker 220, can then be compared to the dose that is actually delivered from the treatment system 10. The comparison of doses after a treatment can be used to detect systematic or random errors in treatment, and prepare for future remedial treatments or treatment modification. In other embodiments, the dose can be monitored by the MOSFET marker 220 throughout the treatment in real-time, and alterations can be made to the delivery strategy during the same treatment.

Figure 6:
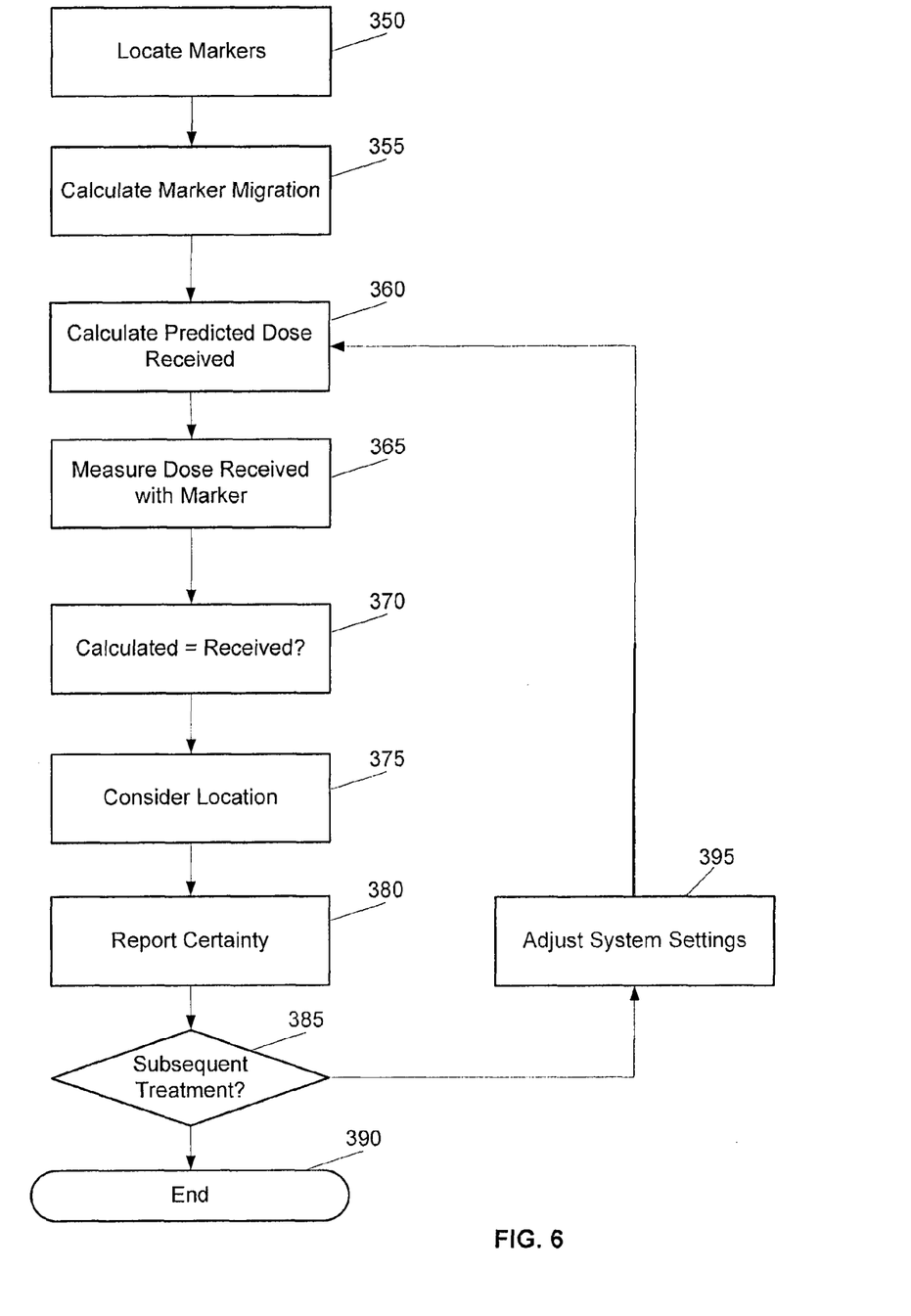
FIG. 6 is a flow chart of a method of utilizing feedback from a MOSFET type marker implanted in, or near a target according to one embodiment of the invention.

FIG. 6 illustrates a flow chart of a method of utilizing feedback from a MOSFET type marker 220 implanted in, or near the target 46. In the embodiment shown in FIG. 6, the process is completed in combination with a daily CT scan, which is completed prior to the treatment being delivered. However, in other embodiments, the markers 220 can be used at any time prior to, during, or after the treatment, and in combination with a variety of other treatments (MRI, PET, etc.).

As shown in FIG. 6, the location of the markers 220 is first determined (block 350). Other beacons and seeds (e.g., the markers 205-215) can also be located to provide a complete set of positional data for the patient 14 and target 46. After locating the markers 205-220, a comparison of their current location can be made to the marker location of past treatments (block 355). In doing so, a migration of the marker 220 (if any) can be tracked. The marker 220 may migrate from one location to another due to outside forces or movement of the target 46. In either case, adjustment may be required if the marker has substantially migrated from one position to another in subsequent treatments. After determining the position of the marker (block 355) the dose that has been delivered by the treatment system 10 can be recorded, and the predicted amount of radiation that was actually received by the patient 14 can be calculated (block 360). The amount and intensity of radiation that has actually been received by the marker 200 can also be measured (block 365).

The predicted dose calculation (block 360) can be compared to the dose that was monitored with the marker 220 (block 365) in order to verify that the dose that was received was equal or near to the dose that was delivered (block 370). After determining whether or not the treatment that was delivered to the patient 14 was equal to the treatment that was received by the patient 14 (block 370) the location of the target 46 can be considered (block 375). The conduciveness of a target 46 to be treated by radiation therapy can vary throughout the body. Therefore, in some cases, the amount of radiation that is delivered by the treatment system 10 can be greater than the dose that is received by the target 46. A report can be generated (block 380) that can indicate, based on prior knowledge of a target 46 and past treatments, the dose that should be received by the patient for a particular delivery. The deformation effects that are likely to occur can also be considered. Using the information of the certainty report and the dose data from the marker 220, the decision can be made whether or not a subsequent treatment is required (block 385). Using the markers 220 in this way can improve deformation calculations and validate projected deformation maps. The process ends if subsequent treatments are not needed (block 390). If another treatment is needed, the settings of the treatment system 10 can be adjusted (block 395) and the process can return to block 360. The position of the components of the treatment system 10 and the dose that is delivered may need to be adjusted based on the type of treatment, deformation, or patient position.

Referring back to FIG. 4, in another embodiment, a set of markers and seeds of the group 200 can be chosen and used to deliver a treatment to a target 10 that is in motion (e.g., a lung, a digestive tract, etc.). The combination of markers and seeds 205-220 that are chosen from the group 200 can be determined according to treatment system 10, the type of treatment that is being delivered, and the patient 14.

In one embodiment, the motion of the target 46 can be tracked using both the group 200 of markers and seeds, as well as with other devices (e.g., fluoroscopy, MVCT, kVCT, and the like). Then, during the delivery of a dose the treatment can be adapted or interrupted depending on the position of the target. For example, the lung of a patient 14 may need to be radiated. Due to the patient's need to breathe during treatment, the target 46 (i.e., the lung) may be in relatively constant motion. To track the motion of the lung, markers and seeds of the group 200 can be implanted in, or positioned proximate to the lung. The motion of the lung can also be monitored by other devices, such as those listed above. By tracking the motion of the lung the treatment that is being delivered can be adapted to include different doses according to the type of motion that is occurring. More specifically, the dose that is being delivered when the patient is breathing in may be different from the dose that is being delivered when the patient is breathing out. Additionally, the motion of the lung and the treatment that is delivered can be verified by comparing the signals of the markers and seeds of the group 200 to the signals of the other devices. If the results of the comparison are not consistent with each other, an error in treatment or an equipment malfunction can be identified. Erratic behavior of the lung (e.g., couching) can also be identified by the markers and seeds of the group 200 so that treatment can be paused or interrupted until the motion becomes more stable.

In another embodiment, the entire collection of devices that are used to track the components of the treatment system 10 and the group 200 of seeds and markers can be used to deliver a treatment to the patient 14. In one such embodiment, the motion of the components of the treatment system 10 and the target 46 are used to provide an optimized treatment using four dimensional, computed tomography (4D CT) images. 4D CT images can refer to a collection of 3D image volumes that each represents a "phase" of a motion pattern, such as breathing. These 4D CT images can be used for contouring, as well as for generating treatment plans that anticipate a certain cycle of phases. However, a patient's motion pattern can often deviate from the ideally reproducible pattern indicated by a 4D CT image set. The seeds and markers of the group 200 can be used to more accurately calculate dose for each of the volumes by monitoring the motion of the patient and/or system components during treatment. The motion that is tracked using the seeds and markers can be irregular or unexpected, and need not follow a smooth or reproducible trajectory. The position of each of the components of the treatment system 10 can also be verified during delivery. Using the measurements acquired by the various devices, an optimal dose can be recalculated for the patient's actual motion pattern. In another embodiment, the motion of the patient 14, the target 46, and the components of the treatment system 10 can be used to recalculate the dose for each phase of the 4D CT in real-time during a treatment. Deformation monitoring techniques (as described above) could also be used as a parameter to calculate and alter the dose between the different phases. Utilizing all of the data sources available can allow an optimized treatment.

Thus, the invention provides, among other things, new and useful systems and methods of determining position of an object and delivering radiation therapy treatment. Various features and advantages of the invention are set forth in the following claims.

What is claimed is:

1. A method of evaluating dose delivered by a radiation therapy system using a device, wherein the device is a marker associated with the patient, the method comprising:
   using a radiation therapy system to deliver radiation to the patient;
   obtaining information relating to the delivery of radiation;
   estimating dose to the marker based at least in part on the information;
   acquiring dose received by the marker; and
   comparing the received dose with the estimated dose.

2. A method as set forth in claim 1 wherein the marker is disposed within the patient.

3. A method as set forth in claim 1 wherein the marker is coupled to the patient and is exterior to the patient.

4. A method as set forth in claim 1 wherein the acquiring act includes receiving a value representing a dose received by the marker and adjusting the value with a calibration value.

5. A method as set forth in claim 1 wherein the obtaining act includes identifying the location of the marker with an image of the patient, and wherein the estimating act further includes calculating dose based at least in part on the location of the marker.

6. A method as set forth in claim 1 wherein the obtaining act includes obtaining motion information for the marker, and wherein the estimating the dose is further based on the motion information.

7. A method as set forth in claim 1 wherein the obtaining act includes obtaining detector data, and wherein the estimating the dose is further based on the detector data.

8. A method as set forth in claim 1 wherein the obtaining act includes obtaining system feedback information, and wherein the estimating the dose if further based on the system feedback information.

9. A method as set forth in claim 1 and further comprising modifying the delivering radiation based at least in part on the comparison.

10. A method as set forth in claim 1 wherein the acquiring act includes acquiring a signal transmitted from the marker having a relation to the intensity of radiation received by the marker.

11. A method as set forth in claim 1 wherein the acquiring act includes acquiring an intensity of a signal being transmitted from the marker.

12. A method as set forth in claim 11 wherein the intensity of the signal being transmitted from the marker is based on an amount of delivered radiation.

13. A method as set forth in claim 1 wherein the acquired act includes at least one of a dose received during a portion of a fraction, a cumulative dose for an entire fraction, and a cumulative dose received over multiple fractions.

14. A method as set forth in claim 1 wherein the estimating act includes performing deformation.

15. A method as set forth in claim 14 wherein the marker is used as a fiduciary point for the performing act.

16. A method as set forth in claim 1 and further comprising determining a position of the marker based at least in part on the comparison.

17. A method as set forth in claim 1 dynamically changing the delivering radiation based on the comparison.

18. A method as set forth in claim 1 and further comprising acquiring motion information for the marker.

19. A method of evaluating dose delivered by a radiation therapy system using a position monitoring device, wherein the position monitoring device is a marker that indicates motion, the marker being associated with the patient, the method comprising:

using a radiation therapy system to deliver radiation to the patient;

monitoring motion of the marker during the delivering radiation;

estimating a dose delivered to the patient based at least in part on the motion of the marker;

acquiring dose received by the marker; and comparing the received dose with the estimated dose.

20. A method as set forth in claim 19 wherein the marker is disposed within the patient.

21. A method as set forth in claim 19 wherein the marker is coupled to the patient and is exterior to the patient.

22. A method as set forth in claim 19 wherein the acquiring act includes receiving a value representing a dose received by the marker and adjusting the value with a calibration value.

23. A method as set forth in claim 19, further comprising identifying the location of the marker with an image of the patient, and wherein the estimating act further includes calculating dose based at least in part on the location of the marker.

24. A method as set forth in claim 19 and further comprising determining a position of the marker based at least in part on the comparison.

* * * * *